United States Patent
Babaev

(10) Patent No.: US 9,486,234 B2
(45) Date of Patent: *Nov. 8, 2016

(54) SURGICAL SAW BLADE

(76) Inventor: Eliaz Babaev, Minnetonka, MN (US)

(*) Notice: Subject to any disclaimer, the term of this patent is extended or adjusted under 35 U.S.C. 154(b) by 49 days.

This patent is subject to a terminal disclaimer.

(21) Appl. No.: 13/021,997

(22) Filed: Feb. 7, 2011

(65) Prior Publication Data

US 2012/0130380 A1 May 24, 2012

Related U.S. Application Data

(60) Provisional application No. 61/303,021, filed on Feb. 10, 2010.

(51) Int. Cl.
*A61B 17/14* (2006.01)
*A61B 17/32* (2006.01)

(52) U.S. Cl.
CPC ....... *A61B 17/320068* (2013.01); *A61B 17/14* (2013.01); *A61B 17/148* (2013.01)

(58) Field of Classification Search
CPC .............. A61B 17/320068; A61B 17/320072; A61B 2017/320072; A61B 17/14; A61B 17/141; A61B 17/148; A61B 2017/320028; A61B 2017/320076

USPC ............ 606/45, 79, 82, 169, 170, 171, 177; 83/835, 846, 847, 854, 855; 600/564, 600/570

See application file for complete search history.

(56) References Cited

U.S. PATENT DOCUMENTS

| 5,423,845 A * | 6/1995 | McDaniel ............. 606/176 |
| 5,935,143 A * | 8/1999 | Hood ................... 606/169 |
| 6,443,969 B1 * | 9/2002 | Novak et al. .......... 606/169 |
| 7,544,200 B2 * | 6/2009 | Houser ................. 606/169 |

* cited by examiner

*Primary Examiner* — Sarah W Aleman
(74) *Attorney, Agent, or Firm* — Winthrop & Weinstine, P.A.

(57) ABSTRACT

This invention discloses methods and devices using an improved surgical saw blade for resecting bone tissue during surgical procedures. The surgical saw blade may be used on oscillating, reciprocating, rotary or vibrational surgical saws. The disclosure describes the use of a cutting blade to resect bone tissue without excessive temperature rise during typical surgical procedures. The cutting blade provides a self-clearing design that includes at least two teeth disposed to prevent accumulation of bone chips within the proximity of the teeth. The design of the cutting blade allows the mechanical motion of the blade and other interactions between the blade and the tissue to remove accumulated bone chips and prevent excessive temperature rise.

13 Claims, 9 Drawing Sheets

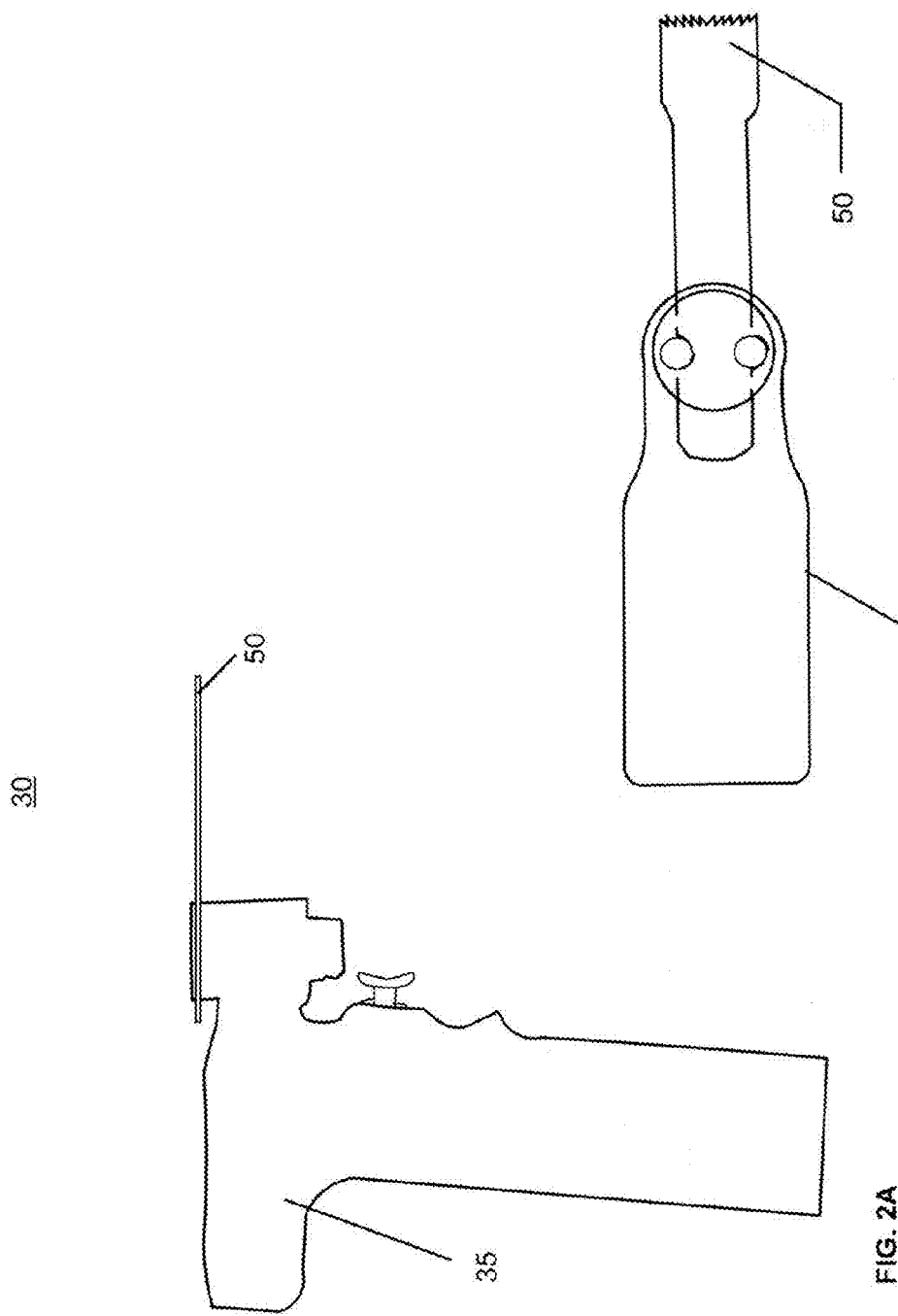

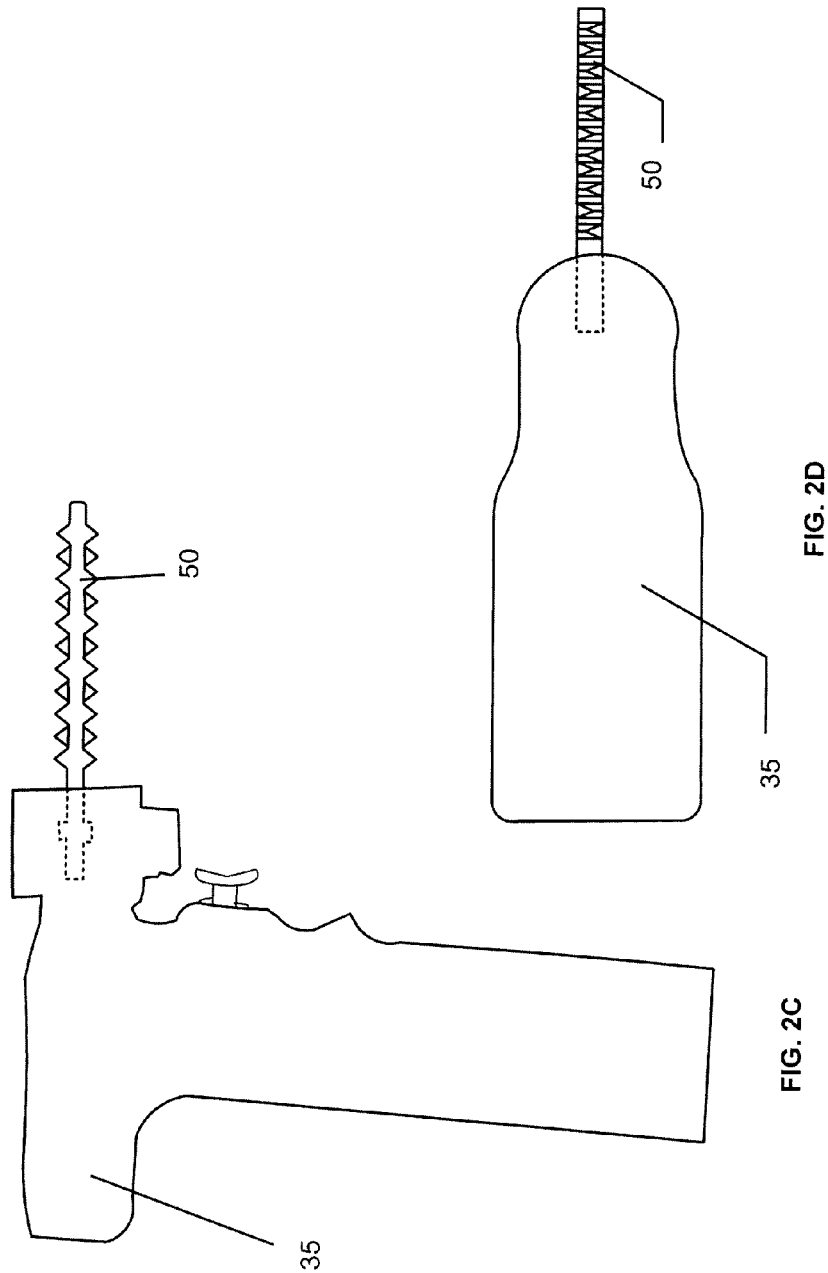

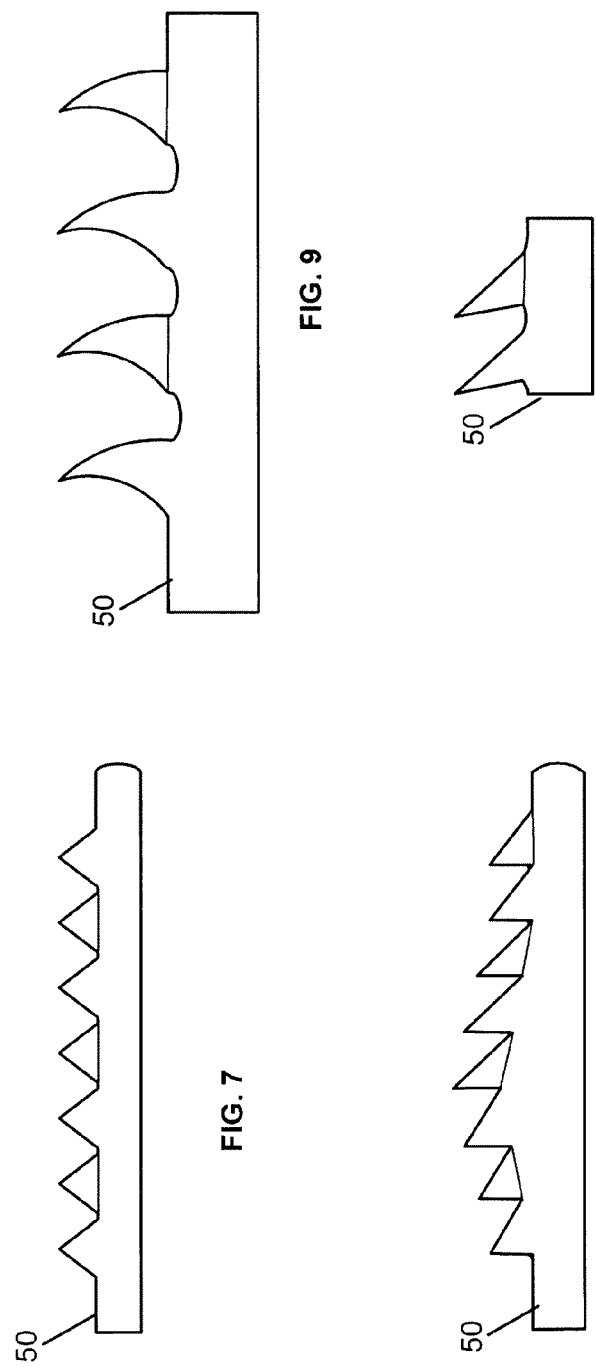

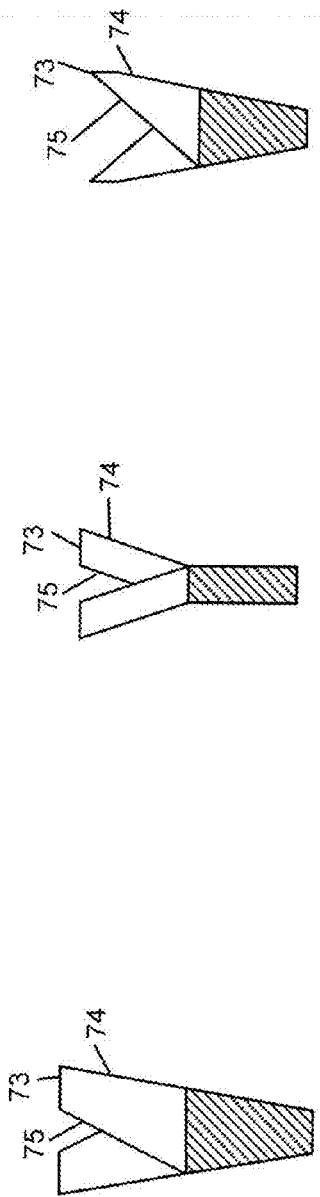

SURGICAL SAW BLADE

BACKGROUND OF THE INVENTION

The following invention relates generally to instrumentalities for cutting bone during surgery. More particularly, the instant invention is directed to a high speed surgical saw which uses a drive mechanism to move a surgical saw blade (cutting blade) back and forth at a high frequency. The drive mechanism is needed to impart a back and forth motion to the cutting blade and may be, for example, a reciprocating, semi-oscillating, rotational or ultrasound drive. The surgical saw blade may have a cutting action in a longitudinal, orthogonal or rotary in relation to the drive mechanism. The surgical saw blade may have a distal portion having at least one pair of teeth configured to be adjacent to each other and each of the pair of teeth having a cutting edge which is oriented with the teeth so that the cutting edge is disposed away from a centrally positioned longitudinal axis between the teeth. A gullet is then formed between the teeth, creating a cavity along the longitudinal axis of the ultrasound horn.

Typical procedures requiring bone removal or resection include surgeries to repair injuries such as orthopedic surgeries or back surgeries, as well as surgeries to access other tissues such as temporary skull resection to access the brain or vertebrae removal to access a spinal cord.

One of the most vexing problems that surgeons face when using ultrasound surgical saws when cutting bone tissue is the rapid temperature rise of the saw blade due to the accumulation of bone chips within the area of the saw teeth. Since tissue necrosis quickly occurs at temperatures greater than 75° C. (degrees centigrade), a rapid temperature rise of an ultrasound surgical saw is a significant problem which may injure or destroy the bone tissue itself as well as other adjacent tissues. The problem is particularly significant since while working the surgeon can neither see nor feel whether he has caused damage, which only becomes subsequently apparent.

When such necrosis occurs, the tissue does not grow into the cut site, fracture site, or surface of the cement-less prosthesis or other prosthesis and may fail to knit. In the absence of knitting, the prosthesis may not be anchored by bone growth, possibly resulting in the necessity to have a replacement operation some period of years thereafter. In some instances, half of all knee or hip operations may be revision procedures, often because in the initial operation, where temperature is a contributing factor, excessive temperatures were reached at the site of the shaped surface or bone kerf (or cut).

An accumulated bone chip grit trapped within the teeth of a saw blade tends to get vibrated at ultrasonic frequencies. This is known to cause the temperature of a saw blade and surrounding tissue to increase very quickly. This effect may limit the use of a device to a maximum period of less than 1-minute before a surgeon must stop cutting to avoid tissue necrosis due to overheating.

SUMMARY OF THE INVENTION

As would be readily apparent to a person of ordinary skill in the art, the disclosed invention would be particularly beneficial to be used for surgeries requiring precision cutting, removing or shaping bone tissue. The invention is directed to a high speed surgical saw which uses a drive mechanism to move a cutting blade back and forth at a high frequency. The drive mechanism used to impart a back and forth motion to the cutting blade may be a purely mechanical device such as a rotary, reciprocating or semi-oscillating drive generally operating at speeds in excess of 20,000 strokes per minute. Generally each type of saw has a unique attachment design requiring a specific geometry. These attachment mechanisms are often slightly different for each manufacturer. The cutting blade of this invention may be readily provided with the required attachment geometry to fit the intended device as a replacement blade. A cutting blade may be directly or indirectly attached to the drive mechanism as described herein. Furthermore, the disclosed methods and devices may also be useful in other applications such as veterinary and autopsy purposes.

For descriptive purposes, the present invention is generally shown as in its ultrasound embodiment. The apparatus comprises an ultrasound generator driving an ultrasound transducer. An ultrasound horn is mechanically coupled to the ultrasound transducer. The ultrasound horn consists of an ultrasound tip or cutting blade and may also include a shaft. The ultrasound horn may also include one or more conduits to provide and/or remove fluids and other materials from the surgical site. The ultrasound horn receives the ultrasound waves from the ultrasound generator and transmits the ultrasound waves to the proximal end of the cutting blade either directly or through the shaft. The shaft and the cutting blade may be integral parts of the ultrasound horn or may be mechanically coupled as one unit.

A housing substantially encompassing the ultrasound transducer and provides a hand piece for convenient holding and manipulating the device. The housing covers the ultrasound transducer and at least portions of the ultrasound horn.

The hand piece may be provided in a variety of configurations. For example, the hand piece may be of a substantially cylindrical shape serving as a grip portion around the longitudinal axis of the ultrasound transducer, or it may be positioned to extend radially from the longitudinal axis of the ultrasound transducer serving as a grip portion having a pistol grip design.

An ultrasound saw will operate at very high rates of speed and with a very short stroke length. The stroke speed is controlled by the ultrasound transducer frequency which may be for example 30,000 strokes per second. The stroke length is controlled by the longitudinal displacement of the ultrasound horn at a particular point, and may be, for example, 80 microns. The high frequency and short stroke length combine to make bone chip ejection a difficult issue to resolve. The accumulation of bone chips then result in friction between the cutting blade and the tissue which generates additional heat. The present invention addresses the problem of rapid heat generation at the cutting blade due to lack of efficient chip removal which is recognized as one cause of excessive heat generation. In surgical situations, such unwanted heat generation is undesirable because of thermal necrosis which damages bone structure adjacent to the cut. Having a cutting edge on a tooth that does not extend across the entire width of the kerf greatly enhances the ability of the cutting blade to clear unwanted bone chips.

In addition to longitudinal movement, the ultrasound horn generates radial energy at points along the ultrasound horn. By controlling teeth geometry, this energy can be focused to assist bone chip removal by directing energy radially from the cutting blade to help move the bone chip material away from the cutting blade.

Furthermore, the present invention allows design of a very thin cutting blade. In addition to allowing for the precision cuts that are desirable for surgical procedures, the thin cutting blade also allows for greater heat dissipation which prevents heat buildup in the blade.

In addition, the plugging of the teeth also results in loss of cutting ability of the saw. Chips of bone that accumulate within the saw kerf and around the saw teeth, prevent the cutting edges of the teeth from contacting the tissue to be cut. This decreases the aggressiveness of the cutting action and may transform the cutting action to an abrading action rather than chipping. This may require the surgeon to apply more hand force to achieve any progress with the cut and may result in additional heat generation as well as increased surgeon fatigue.

Another problem noted in existing blades involves the tendency of the saw to initially wander rather than to form a kerf. This may be a desirable feature in a device used for shaping bone, but is problematic when a surgeon desires a precise cut at a precise location. In the invention, a temporary a center bone ridge located in the gullet between adjacent teeth is used to help guide and stabilize the cutting blade The gullets between adjacent teeth are open to each other to form a continuous cavity along the longitudinal axis of the cutting blade. In its essence, the blade of the invention takes into consideration the natural tendencies at play when a surgeon is cutting a bone with an ultrasound surgical saw. In general, the cutting action is parallel to the longitudinal axis of the ultrasound horn. The geometric design of the teeth, in cooperation with the ultrasound energy being emitted from the surfaces and edges of the teeth, cooperate to eject bone chips laterally from the cutting edges using the radial energy from the ultrasound horn.

Typically very thin cuts are desired during bone surgery. By minimizing the kerf, faster healing is promoted since a patient's body needs to generate less tissue to heal. One attribute of the instant invention is that each working tooth cooperatively cuts some material with its adjacent working tooth so that collectively, the teeth make progressive contributions to generate a kerf that may achieve a desired width of approximately 1 mm.

Accordingly, it is the primary object of the present invention to provide a novel and useful surgical saw blade for use in open surgery as well as minimally invasive, cannula based surgical techniques.

A further object of the invention is to provide a surgical saw blade that may be utilized by a variety of drive mechanisms.

A further object of the invention is to provide a surgical saw blade that may be manufactured as a disposable component of a surgical saw system.

A further object of the present invention is to provide a device as characterized above which minimizes the degree of heat buildup associated with the surgical cutting to reduce the thermal necrosis that attends cutting bone.

A further object of the present invention is to provide a device as characterized that reduces buildup of bone chips within the saw kerf and between the saw teeth using a self-clearing design to clean out the saw kerf.

A further object of the present invention is to provide a device as characterized above which can be relatively economically manufactured, lends itself to mass production techniques and is extremely durable in construction.

A further object of the present invention is to provide a device as characterized above which cuts aggressively and has a tendency to initially form a kerf, and self centers itself and cuts through the bone quickly within which the blade will reside.

A further object of the present invention is to provide a surgical saw blade having a centrally positioned longitudinal axis, a proximal end (proximal meaning closest to surgeons handpiece or normal gripping position) configured to couple to an ultrasound horn and a distal end (farthest from surgeons handpiece) having at least one pair of teeth having tips for cutting bone which are configured to be adjacent to each other and wherein each tooth have a cutting edge less than the width of the kerf, the pair cooperating to form the kerf.

Another aspect of the invention is to provide a device with teeth positioned along the radial surface of an ultrasound horn, substantially parallel to the ultrasound horn's longitudinal axis.

Another aspect of the invention is to provide a device with an ultrasound transducer and an ultrasound horn positioned along a similar longitudinal axis. Another aspect of the invention is to provide a device with an ultrasound horn having a conduit for providing or removing a fluid to the surgical site.

BRIEF DESCRIPTION OF THE DRAWINGS

FIG. 2a depicts a side view of one embodiment of the surgical saw blade in an oscillating mechanical drive.

FIG. 2b depicts a plan view of one embodiment of the surgical saw blade in a oscillating mechanical drive.

FIG. 2c depicts a side view of one embodiment of the surgical saw blade in a reciprocating mechanical drive.

FIG. 2d depicts a plan view of one embodiment of the surgical saw blade in a reciprocating mechanical drive.

FIG. 7 depicts a side view of an alternative embodiment of the cutting blade.

FIG. 8 depicts a side view of an alternative embodiment of the cutting blade.

FIG. 9 depicts a side view of an alternative embodiment of the cutting blade.

FIG. 10 depicts a side view of an alternative embodiment of the cutting blade.

FIG. 11 depicts a cross sectional view of an alternative embodiment of the cutting blade.

FIG. 12 depicts a cross sectional view of an alternative embodiment of the cutting blade.

FIG. 13 depicts a cross sectional view of an alternative embodiment of the cutting blade.

FIG. 14 depicts a cross sectional view of an alternative embodiment of the cutting blade.

FIG. 15 depicts a cross sectional view of an alternative embodiment of the cutting blade.

DETAILED DESCRIPTION OF THE INVENTION

The present invention relates to a surgical saw blade 50 for use with a surgical saw 10 for use during surgical procedures. Several embodiments and details of the invention are shown in FIGS. 1-15 and described herein. The disclosure describes the apparatus and methods in reference to surgical procedures on bones, however the invention is appropriate for other surgical procedures generally.

Figure 1:
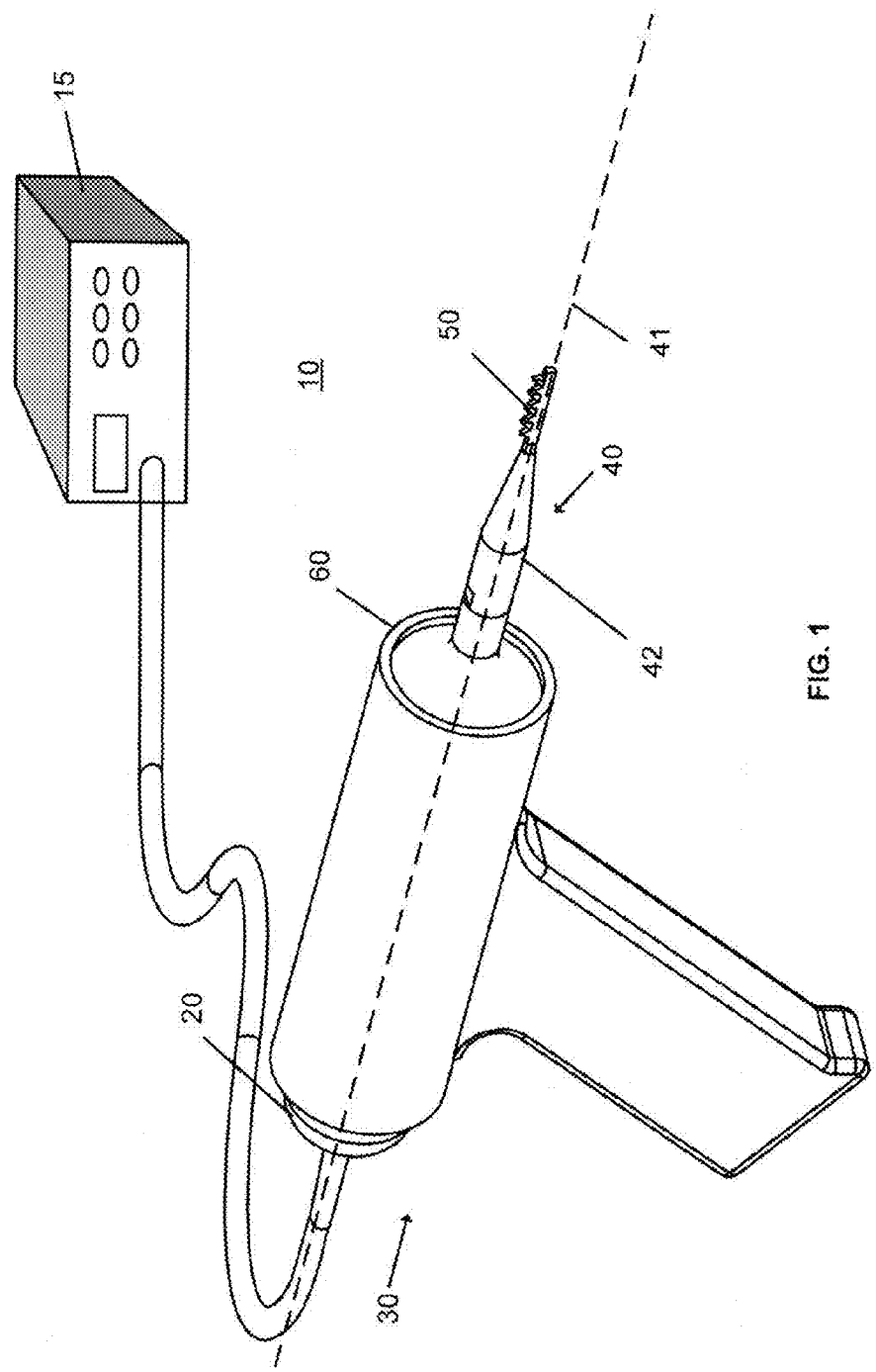
FIG. 1 depicts a perspective view of one embodiment of the surgical saw blade with an ultrasound apparatus.

FIG. 1 depicts one possible embodiment of the surgical saw 10 of the present invention. The depicted embodiment comprises an ultrasound generator 15 with an electrical cord supplying the ultrasound generator 15 its power, such as standard AC or battery power. The ultrasound generator 15 is in electrical communication with an ultrasound transducer 20 through a signal connector. A power switch may be provided to activate the surgical saw 10. The switch, for example, may be foot activated or a trigger or button located on the handpiece or generator.

Figure 3:
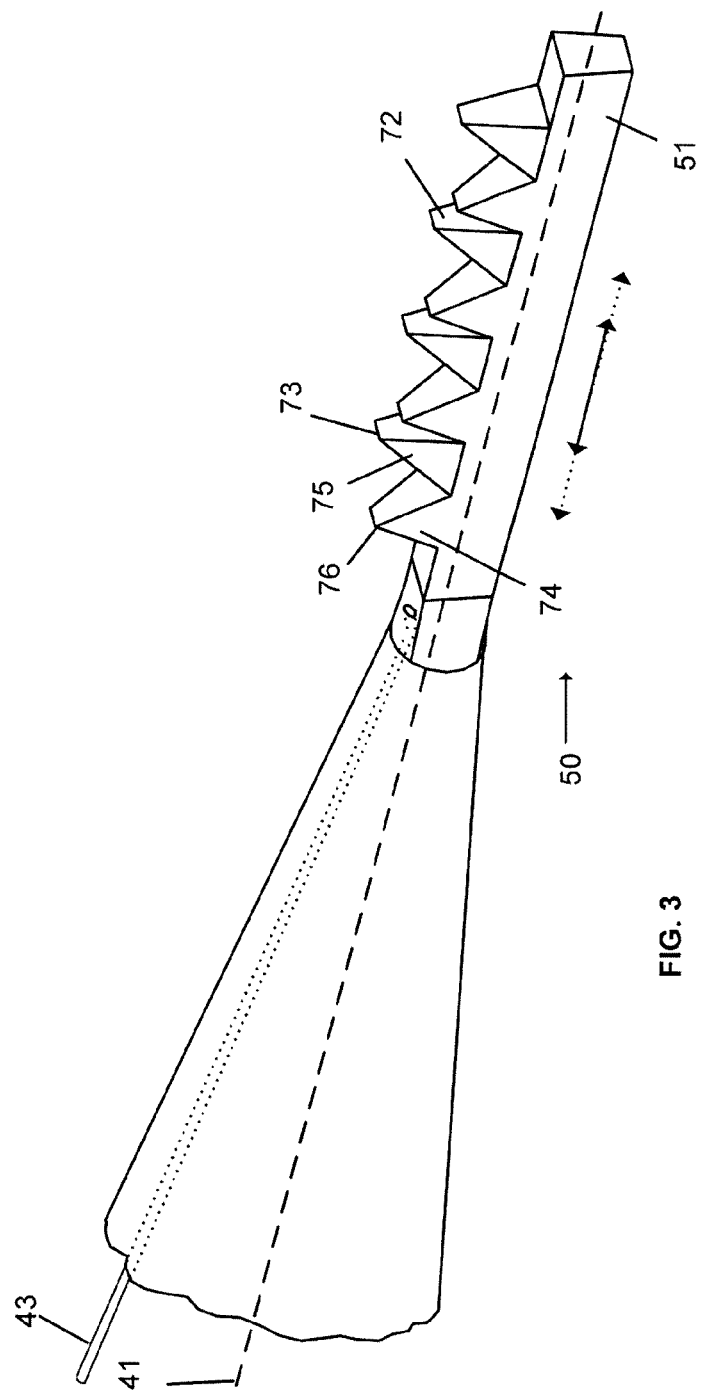
FIG. 3 depicts a perspective view of one embodiment of the cutting blade.

As shown by example in FIGS. 1 and 2, the handpiece 30 may be in various embodiments. A surgeon manipulates hand piece 30 containing an ultrasound transducer 20, a housing 35, an ultrasound horn 40 and optionally a shield 60. The ultrasound transducer 20 is driven by the ultrasound generator 15. The housing 35 surrounds the ultrasound transducer 20 and provides a gripping surface. The housing 35 may cover portions of the ultrasound horn 40. The ultrasound horn 40 is connected to the distal end of the ultrasound transducer 20 along a longitudinal axis 41. Placing the ultrasound horn 40 and the ultrasound transducer 20 along a longitudinal axis 41, increases the efficiency of the ultrasound transmission through the ultrasound horn 40 and reduces the chances of metal cracking or breaking within portions of the ultrasound horn 40 such as at the cutting blade 50 at the ultrasound tip. This can be a severe problem due to the high operating frequency and thin width of the cutting blade 50 that are preferred. The ultrasound horn 40 includes at least a cutting blade 50 and may include a shaft 42 disposed between the cutting blade 50 and the ultrasound transducer 20. The ultrasound horn 40 may optionally include one or more conduits 43 as shown in FIG. 3 for adding a fluid to the surgical site or removing (aspirating) fluid from the surgical site. Openings between and among the teeth may allow movement of fluid along the length of the cutting blade. Additional conduits and/or channels may be provided on the cutting blade 50 to further distribute the fluid. The use of a channel for aspirating fluids would include removing blood, other body fluids or added fluids that generally accumulate at a surgical site. Examples of possible uses for the addition of fluids include supplement cooling, lubrication or therapeutic purposes.

A shield 60 optionally attached to the housing 35 covers at least portions of the ultrasound horn 40 to prevent undesirable contact between the ultrasound horn 40 with the patient's tissue and/or surgeon's hand. The shield 60 may extend the entire length of the cutting blade 50 with an opening exposing the teeth 70 of the cutting blade 50. The shield 60 may be rigid or flexible material such as aluminum or various plastic materials as well as of a disposable or sterilizable design.

The ultrasound generator 15 and ultrasound transducer 20 are well known in the art and will not be described in detail herein. However, control of the electrical signal directly influences the ultrasound wave properties and allows optimization of the ultrasound treatment particularly with respect to the ultrasound thermal, cavitation and microstreaming properties. The ultrasound generator 15 should be capable of producing an electrical signal of a sufficient alternating voltage to drive the ultrasound transducer 20 and to achieve the desired therapeutic effect. The ultrasound transducer 20 converts the alternating voltage into mechanical motion as to induce a shaft 42 to vibrate. The shaft 42 transmits the ultrasonic vibrations to the ultrasound tip with cutting blade 50 to induce vibrations. The amplitude of the vibrations is typically between approximately 1 micron and approximately 300 microns. The preferred amplitude range is approximately 60 microns-100 microns. The recommended amplitude value is approximately 80 microns.

The magnitude of the longitudinal ultrasonic vibrations provides the mechanical energy to move the cutting blade 50 back and forth along the longitudinal axis 41. The geometric conformation of the teeth and the position of the teeth relative to each other assist with the self-clearing properties of the cutting blade 50.

During use of the handpiece 30 the electrical signal produced by ultrasound generator 15 should also be sufficient to drive the ultrasound transducer 20 to induce the cutting blade 50 stroke frequency to vibrate approximately in resonance at any frequency within the ultrasound spectrum, such as, but not limited to, between approximately 15 kHz and approximately 3 mHz. The preferred frequency range for the cutting blade 50 is 15 kHz to 50 kHz with a recommenced frequency of approximately 30 kHz. The ultrasound generator 15 may have multi-frequency capabilities to operate at selectable alternative frequencies within the ranged utilized.

The ultrasound transducer 20 may be driven with a continuous wave or pulsed frequency signal supplied by ultrasound generator 15. Driving transducer 20 with a continuous wave tends to induce the release of standing waves from the various surfaces of the cutting blade 50, while a pulsed frequency reduces or avoids the release of standing waves. The pulsed frequency signal generates less heat, cavitation and streaming currents, and may increase the longitudinal force of the induced vibrations as a result of the on/off cycle changes. The electrical signal may be changed depending on the desired features of the released ultrasound waves for the particular application. For example, inducing the release of standing waves from the cutting blade 50 may be helpful to produce or increase cavitation effects and thereby self-cleaning properties. The wave form of the electrical signal may be sinusoidal, rectangular, trapezoidal and/or triangular. In addition, the electrical signal from the ultrasound generator 15 may be fixed or modulated to allow ultrasonic wave amplitude variability. The ultrasound generator 15 may include feedback control to adjust the signal.

To conduct bone surgery requires access to the patient's tissue beneath the surface of the skin. This can be accomplished through open surgery by an incision through the skin, muscle and other tissues to access the bone. The access may be completed with this or other tools. It may also by accomplished by minimally invasive techniques were the patient's tissue is accessed through skin punctures and the surgery is conducted through cannula based narrow diameter instruments, with cameras and/or other sensors being used for visualization.

A housing 35 serving as a handle for the ultrasound device isolates the vibrations of ultrasound transducer 20 from being transferred to the surgeon holding the device. Operators of the ultrasound device can hold the housing 35 during use to manipulate the device. The housing 35 provides a surface appropriate for hand manipulation by the surgeon and/or user while allowing the user to avoid direct contact with vibrations within the device. The housing may extend over the entire ultrasound transducer 20 and/or may partially enclose portions of the shaft 42. FIG. 1 shows the housing 35 incorporating a grip portion similar to a pistol grip configuration oriented radial to the longitudinal axis. The pistol grip may provide for increased visibility to the surgical site area during use of the hand piece 30.

The ultrasound horn 40 may include a shaft 42 and a cutting blade 50 all driven by the ultrasound transducer 20.

The cutting blade 50 may be integral with or mechanically coupled to a shaft 42 or directly to the ultrasound transducer 30. The shaft 42 and cutting blade 50 connections may be completed by threading, welding and/or other means readily recognizable by people of ordinary skill in the art. The ultrasound horn 40, or portions of the ultrasound horn 40, may be removable from the hand piece for cleaning, sterilization and/or replacement as would be understood by those skilled in the art upon review of this disclosure. The shaft 42 and cutting blade 50 may be fabricated from metals such as, but not limited to, alloys of titanium, aluminum and/or steel. The cutting blade 50 may be fabricated as a one-use disposable embodiment as an alternative to a sterilizable embodiment. To prevent premature material failure, the cutting blade 50 manufacture preferably does not include material bending, such as such as setting teeth angles by bending during cutting blade fabrication. Preferably the cutting blade 50 is manufactured by molding, casting or cutting operations as readily known in the art.

The cutting blade 50 has a preferred thickness of 1 mm. (millimeter). The range of thickness is typically from 0.1 to 10 mm. with the higher thickness blade often utilized for precision bone shaping applications, rather than precision cutting requiring a narrow kerf.

FIG. 2A depicts a side view of one embodiment of the surgical saw blade 50 in a surgical saw 10 using an oscillating mechanical drive.

FIG. 2B depicts a plan view of one embodiment of the surgical saw blade 50 in a surgical saw 10 using an oscillating mechanical drive. Typical prior art oscillating saws compatible with this surgical saw blade 50 include Styker System 6 Precision sagittal saw, Conmed Linvatec Model PR06300 and MicroAire Surgical Instruments Model 7506.

FIG. 2C depicts a side view of one embodiment of the surgical saw blade 50 in a surgical saw 10 using a reciprocating mechanical drive. Typical prior art reciprocating saws compatible with this surgical saw blade 50 include Styker System 6 Precision reciprocating saw, Conmed Linvatec Model PR06400 and MicroAire Surgical Instruments Model 7507.

FIG. 2D depicts a plan view of one embodiment of the surgical saw blade 50 in a surgical saw 10 using a reciprocating mechanical drive.

The saw blade 50 may also have a circular geometry with the cutting edge along the circumference mounted on a conventional rotatable mechanical drive similar to a grinder or drill.

Figure 4:
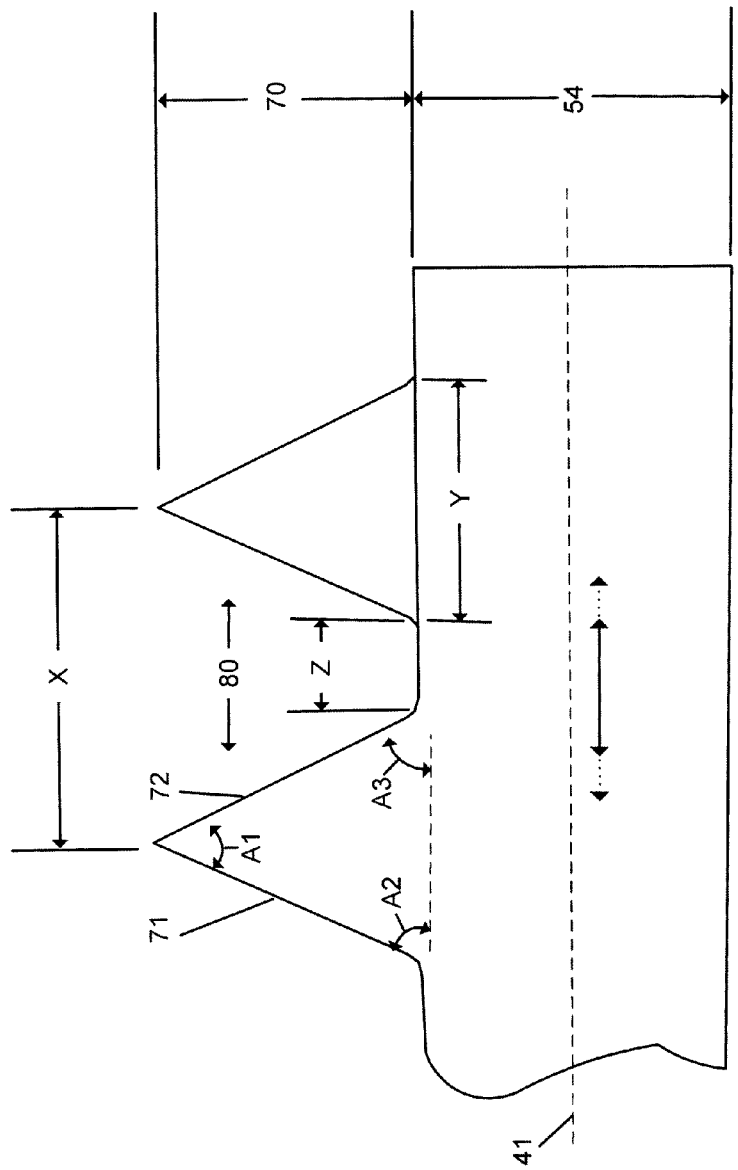
FIG. 4 depicts a side view of an alternative embodiment of the cutting blade.

As shown in FIG. 3 (perspective view) and FIG. 4 (side view), the optional shaft 42 portion of the ultrasound horn 40 may have a longitudinal axis 41. The shaft 42 is shown with a proximal section attached to the ultrasound transducer 30 and a distal section attached to the cutting blade 50 portion of the ultrasound horn 40. A radial perimeter on the outer surface of the shaft 40 provides an entry/exit port for the conduit 43. In a preferred embodiment, to prevent premature metal fatigue between the ultrasound horn 40 and the ultrasound transducer 20 and to provide efficient transmission of the ultrasound waves, the longitudinal axis 41 of the ultrasound horn is substantially co-linear with the longitudinal axis of the ultrasound transducer 20.

The cutting blade 50 provides a support structure 54 to support a plurality of teeth 70. The support structure 54 may be, for example, a rectangular or trapezoidal design. The support structure 54 at its proximal end is attached to the ultrasound horn 40 at its distal end. The support structure 54 would generally have a free distal end. It also may be curvilinear around its radial perimeter. The width of the support structure 54 is typically less than or equal to the maximum width of the cutting blade 50 to avoid severely limiting the depth of a cut. Preferably, the support structure 54 is narrower than the maximum width of the cutting blade 50. The radial edge along which the teeth 70 are attached is preferably substantially parallel with the longitudinal axis 41. The teeth 70 may be mounted along a curvilinear radial edge with a maximum angle of less than 45 degrees.

The teeth 70 are typically arranged in pairs with each tooth cutting a portion of the cut, with at least one pair of adjacent teeth 70 defining the total width of the cut. The teeth 70 emerge from a radial surface of the ultrasound horn 40 at the interface with the support structure 54 having a proximal face 71 and a distal face 72 forming angles with the support structure identified as proximal face angle A2 and distal face angle A3 respectively.

The proximal face 71 and distal face 72 meet to form a cutting edge 73 along a vertex 76 having a vertex angle A1. Vertex angle A1 is preferably 60 degrees, but may vary from 10 to 170 degrees.

Figure 5:
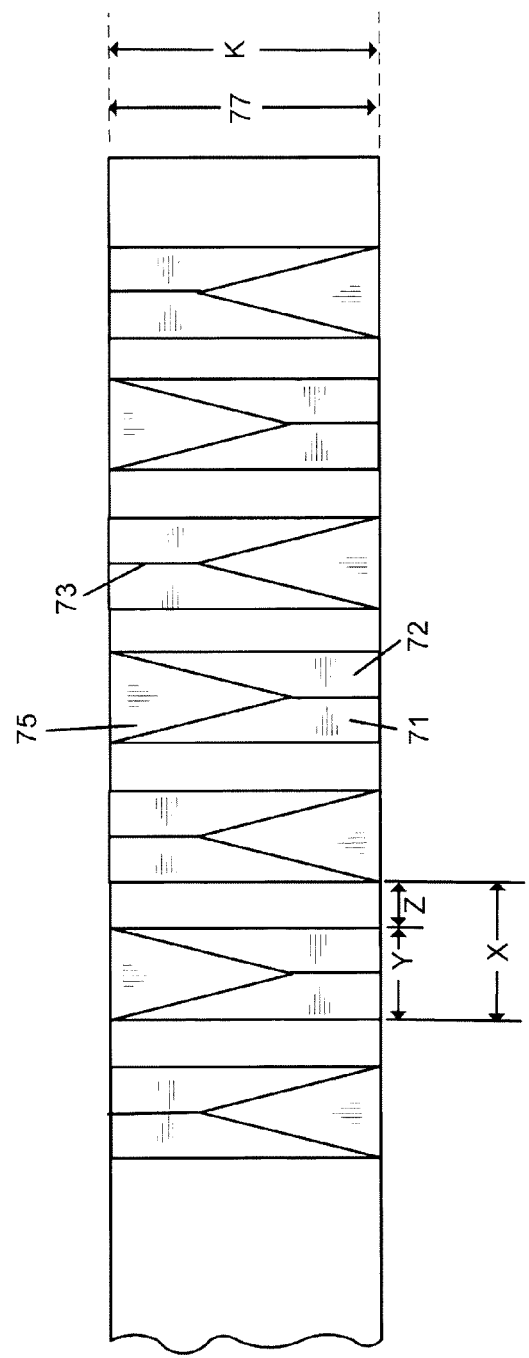
FIG. 5 depicts a top plan view of an embodiment of the cutting blade.

As shown in FIGS. 3 and 5, the teeth 70 may be arranged along the longitudinal axis 41 with a tooth width Y and a tooth gap Z between adjacent teeth 70 resulting in a tooth spacing X. The length of Z may vary from 0 to 10 mm. with lengths less than 0.1 mm. preferred. The intersection of the tooth with the support structure 54 is preferable slightly rounded to reduce the potential for stress cracking at the intersection. The cutting edge 70 produces a kerf 77 defined by the width of the cutting edge 70 at its widest point. Kerf 77 having a width K is preferably 1 mm. with a range between 0.1 and 10 mm.

Figure 6:
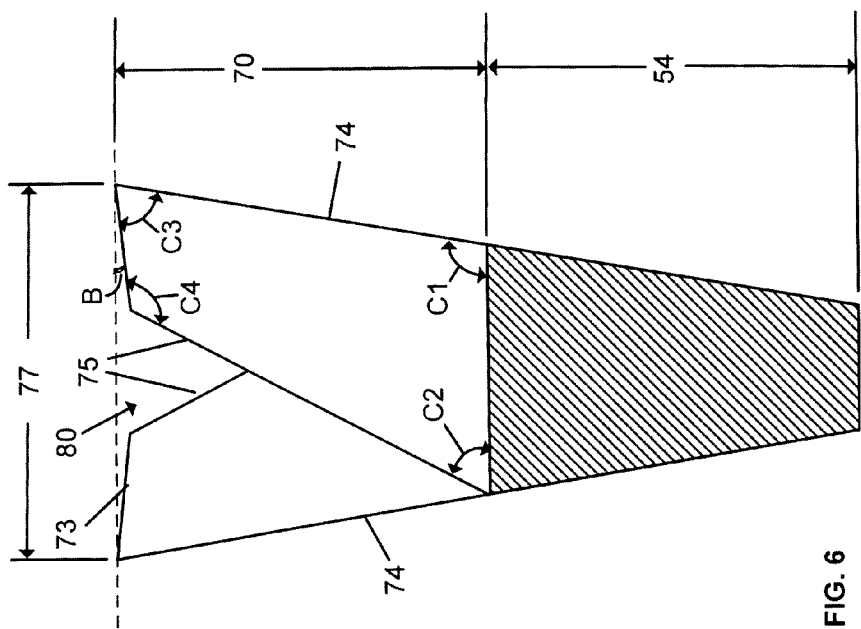
FIG. 6 depicts a cross sectional view of an alternative embodiment of the cutting blade.

With reference to FIGS. 3 and 6, FIG. 6 shows a cross section revealing portions of a pair of teeth. As shown, although each tooth 70 has an exterior face 74 and an interior face 75 originating from the support structure 54, the relative position alternates with each tooth from the right side to the left side. The exterior face 74 intersects with support structure 54 forming a lower outer side angle C1. The interior face 75 intersects with the support structure 54 forming a lower inner side angle C2. Preferably the lower outer side angle is greater than the lower inner side angle.

The interior face 75 and exterior face 74 of a tooth intersect at a cutting edge 73. The cutting edge 73 is preferably ⅓ of kerf 77 width K. The cutting edge 73 may be horizontal and parallel to the base of the tooth, or it may form an angle B with a horizontal projection of the cutting edge. The horizontal projection of cutting edge 73 may vary from 0 mm. to any dimension up to the width of the kerf 77. At 0 mm. the cutting edge 73 is simply a point, and the interior face 75 and the exterior face 74 intersect at the point of the cutting edge 73. The cutting edge 73 forms an upper outer side angle C3 where it intersect with the exterior face 74 an upper inner side angle C4 where it intersects with the interior face 75.

Cutting of a bone surface occurs on the cutting edge 73 of the teeth 70, the interior face 75 of the teeth 70 and to some extent on the exterior face 74 of the teeth. As a result, it is generally preferable to have a maximum width of the cutting blade 70 along the cutting edge 73.

While the opposing exterior faces 74 of adjacent teeth generate the saw kerf 77 at their widest dimension. The opposing interior faces 75 of adjacent teeth form a gullet 80 that extends between each pair of teeth within the saw kerf 77. The adjacent gullets 80 defined by the teeth 70 are interconnected among each other over the length of the cutting blade 70 to form a cavity along the cutting blade 70 that is substantially parallel to the longitudinal axis 41.

Although adjacent teeth are shown as opposing mirror images, this is not required. To change gullet 80 geometry, it is possible to have an adjacent tooth somewhat smaller than another, or with a different described angle than the other.

The gullet 80 is an interconnected cavity running substantially parallel along the longitudinal axis 41 of the cutting blade 50 between the teeth 70. It is the gullet that defines the space for bone chips to pass to be ejected from the saw kerf 77. The gullet 80 also provides passages to distribute fluid along the cutting blade 50. The gullet 80 may also define a ridge within the kerf 77 that allows temporary support for faces of the teeth 70. This enhances stability which is particularly beneficial when starting precision cutting.

Chip ejection from the gullet 80 is of course defined by the geometry of the teeth, but also the spacing of the teeth and the gap between the teeth to produce a self-clearing design. Increasing the gap between the teeth provides for easier ejection of the bone chips.

In addition to the mechanical ejection to assist chip ejection due to the cutting blade vibrations from the longitudinal vibrations of the ultrasound horn 40, the radial energy component of the ultrasound energy may be used to assist bone chip ejection. At each geometric intersection of the teeth 70 along the cutting blade 50, the ultrasound waves may focus and/or concentrate ultrasonic energy. The emission of this energy may be used to move the bone chips from the gullet 80 or away from a tooth surface. For example, at the intersection of the various faces of the tooth 70 and intersection between the support structure 54 and the tooth 70 ultrasound waves may be concentrated and emitted. These waves may then assist the mechanical action to eject bone chips from within the vicinity of the cutting blade 50 and away from the kerf 77 itself.

Removing the bone chips from the vicinity of the cutting blade 50 prevents the cutting action of the cutting blade 50 from becoming an abrasive cutting action. This allows the bone tissue to remain at temperatures less than 75° C. which is a critical temperature for necrosis. Generally, with the use of this invention temperatures can be maintained at levels below 55° C.

FIG. 7 depicts a side view of an embodiment of the cutting blade 50 showing alternating teeth with a rounded tooth gap between the teeth 70 with interior and exterior faces forming isosceles triangle shapes.

FIG. 8 depicts a side view of an embodiment of the cutting blade 50 showing alternating teeth with forming right angles with a proximal face angle A2 perpendicular to the longitudinal axis 41. The teeth 50 are mounted along a curvilinear support structure while maintaining an overall configuration substantially parallel to the longitudinal axis.

FIG. 9 depicts a side view of an alternative embodiment of the cutting blade having curvilinear distal face 72 and proximal face 71 rather than a triangular face.

FIG. 10 depicts a side view of an alternative embodiment of the cutting blade having the cutting edge 73 positioned proximally to the remainder of the tooth 70 having the proximal face angle A2 greater than 90 degrees.

As shown in FIGS. 7-10, the although the cutting blade 50 may have a longitudinal axis 41 it is not required that all radial surfaces of the support structure 54 necessarily be parallel to the longitudinal axis 41, or that the cutting edges 53 be equidistance from the longitudinal axis 41.

FIG. 11 depicts a cross sectional view of an alternative embodiment of the cutting blade 50 having a horizontal cutting edge 73 and the exterior face 74 on an imaginary plane being an extension of the imaginary plane of the support structure radial surface.

FIG. 12 depicts a cross sectional view of an alternative embodiment of the cutting blade 73 having the exterior face 74 on a different plane from the support structure radial surface.

FIG. 13 depicts a cross sectional view of an alternative embodiment of the cutting blade 73 forming a point at the intersection of the exterior face 74 and interior face 75 and also having the exterior face 74 with an interior angle.

FIG. 14 depicts a cross sectional view of an alternative embodiment of the cutting blade 73 having a curvilinear exterior face 74 and the support structure having a curvilinear radial perimeter.

FIG. 15 depicts a cross sectional view of an alternative embodiment of the cutting blade 73 having the exterior face 74 with an interior angle.

As shown within these example cross-sectional diagrams of FIGS. 11-15, the kerf width is determined by the width of the cutting blade 50 at the cutting edge 73 or alternate teeth 70.

Although specific embodiments of apparatuses and methods using the apparatus as an example, have been illustrated and described herein, it will be appreciated by those of ordinary skill in the art that any arrangement, combination, and/or sequence that is calculated to achieve the same purpose may be substituted for the specific embodiments shown. It is to be understood that the above description is intended to be illustrative and not restrictive. Combinations of the above embodiments and other embodiments as wells as combinations and sequences of the above methods and other methods of use will be apparent to individuals possessing skill in the art upon review of the present disclosure.

The scope of the claimed apparatus and methods should be determined with reference to the appended claims, along with the full scope of equivalents to which such claims are entitled.

I claim:

1. An apparatus for use in surgery comprising:
    an ultrasonic surgical saw with a drive mechanism;
    a cutting blade attached to the drive mechanism;
    the cutting blade having a support structure holding a plurality of teeth arranged on a surface, the surface defining a horizontal plane and extending parallel to a longitudinal axis;
    the teeth extending upwardly from the surface and having a cutting edge extending substantially horizontally and partially across the width of the cutting blade in a direction substantially orthogonal to the longitudinal direction;
    the teeth arranged in pairs, wherein the teeth in each pair lie on different planes orthogonal to the longitudinal axis of the blade;
    the teeth in each pair diverging as they extend from the surface to the cutting edge, forming a kerf wider than the support structure; and
    a gullet extending parallel to the longitudinal axis and between each pair of teeth interconnecting all teeth along the longitudinal axis.

2. The apparatus according to claim 1 wherein the cutting blade has a width less than 1-millimeter.

3. The apparatus according to claim 1 wherein the drive mechanism also has a conduit for transferring a fluid.

4. The apparatus according to claim 1 characterized by an ultrasound transducer being capable of inducing an ultrasound horn to vibrate approximately in resonance at a frequency between approximately 15 kHz and approximately 3 mHz.

5. The apparatus according to claim 1 characterized by an ultrasound transducer being capable of inducing an ultrasound horn to vibrate approximately in resonance at a frequency of approximately 30 kHz.

6. The apparatus according to claim 1 producing an electrical signal of a voltage sufficient to induce the ultrasound horn to vibrate approximately in resonance with the amplitude of the vibrations being between approximately 1 micron and approximately 100 microns.

7. The apparatus according to claim 1 wherein the characterized by the generator being capable of producing an electrical signal of a voltage sufficient to induce the ultrasound horn to vibrate approximately in resonance with the amplitude of the vibrations being approximately 80 microns.

8. The apparatus of claim 1 wherein the housing has a grip portion having a substantially axial configuration along a longitudinal axis.

9. The apparatus of claim 1 wherein the housing has a grip portion in a pistol grip configuration radial to a longitudinal axis.

10. The apparatus of claim 1, wherein each tooth has an exterior face and an interior face, and wherein the exterior face of each tooth in each pair of teeth diverge as the teeth extend from the support structure to the cutting edge.

11. The apparatus of claim 10, wherein the diverging exterior faces of each tooth in each pair of teeth extend upward and outward at the same angle as the support structure, each exterior surface forming a straight line with the support structure.

12. An apparatus for use in surgery comprising:
a drive mechanism communicating with a cutting blade;
the cutting blade having a high frequency vibration along the longitudinal axis;
the cutting blade also having a support structure holding a plurality of teeth arranged on a surface, the surface defining a horizontal plane and extending parallel to a longitudinal axis;
the teeth extending upwardly from the surface and having a cutting edge extending substantially horizontally and partially across the width of the cutting blade in a direction substantially orthogonal to the longitudinal direction;
the teeth arranged in pairs, wherein the teeth in each pair lie on different planes orthogonal to the longitudinal axis of the blade;
the teeth in each pair diverging as they extend from the support structure to the cutting edge, forming a kerf wider than the support structure; and
a gullet extending parallel to the longitudinal axis and between each pair of teeth interconnecting all teeth along the longitudinal axis.

13. A self-clearing cutting blade for use in surgery comprising:
the cutting blade disposed along a longitudinal axis;
the cutting blade having a support structure holding a plurality of teeth arranged on a surface, the surface defining a horizontal plane and extending parallel to a longitudinal axis;
the teeth arranged in pairs, wherein the teeth in each pair lie on different planes orthogonal to the longitudinal axis of the blade;
the teeth extending upwardly from the surface and having a cutting edge extending substantially horizontally and partially across the width of the cutting blade in a direction substantially orthogonal to the longitudinal direction;
the teeth in each pair diverging as they extend from the support structure to the cutting edge, forming a kerf wider than the support structure; and
a gullet extending parallel to the longitudinal axis and between each pair of teeth interconnecting all teeth along the longitudinal axis.

* * * * *